United States Patent [19]
Bargigia et al.

[11] Patent Number: 4,748,282
[45] Date of Patent: May 31, 1988

[54] PROCESS FOR THE SYNTHESIS OF MONO-DI-HYDROXYFLUORO-ALKANES

[75] Inventors: Gianangelo Bargigia; Claudio Tonelli; Vito Tortelli, all of Milan, Italy

[73] Assignee: Ausimont S.p.A., Milan, Italy

[21] Appl. No.: 55,061

[22] Filed: May 28, 1987

[30] Foreign Application Priority Data

May 30, 1987 [IT] Italy ................................ 20655 A/86

[51] Int. Cl.$^4$ ............................................. C07C 31/38
[52] U.S. Cl. ..................................................... 568/842
[58] Field of Search ......................................... 568/842

[56] References Cited

U.S. PATENT DOCUMENTS 4,001,309  1/1977  Hayashi et al. ...................... 568/842
4,219,681  8/1980  Schwenk et al. .................... 568/842

Primary Examiner—Howard T. Mars
Attorney, Agent, or Firm—Stevens, Davis, Miller & Mosher

[57] ABSTRACT

A process for preparing mono- and di-hydroxyfluoroalkanes which comprises reacting in a homogeneous phase the corresponding iodo-fluoroalkanes with water in an organic solvent, completely miscible with water or in which water is soluble for at least 1.7% by weight at 20° C., and in the presence of catalysts comprising one or more transition metal ions, at temperatures ranging from 120° to 280° C.

5 Claims, No Drawings

PROCESS FOR THE SYNTHESIS OF MONO-DI-HYDROXYFLUORO-ALKANES

BACKGROUND OF THE INVENTION

The present invention relates to the preparation of mono and di-hydroxyfluoroalkanes starting from the corresponding iodofluoroalkanes.

According to known processes for the synthesis of fluoroalkanols of the above-mentioned type which start from the corresponding iodides, for example oleum is used as a hydrolizing agent (U.S. Pat. No. 3,283,012). In this case there is the serious drawback of the removal of a considerable excess of $H_2SO_4$; furthermore, the recovery of iodine is complex and by-products such as ethers or olefins ca easily form.

A later process (DOS No. 3,016,571) is based on a reaction in a two-phase liquid system, comprising a phase transfer catalyst and/or perfluorocarboxylic surfactants, the process comprising the step of reacting fluoroiodoalkanes with stoichiometric amounts of salts of Cu, Ag, Hg or with an excess thereof.

Some drawbacks of this method are the possible forming of emulsions difficult to be treated, the use of high amounts of the abovesaid salts which must then be recovered, as well as of expensive ingredients such as the phase transfer catalysts.

A further patent (DOS No. 3,035,641) claims a process for the preparation of alkanols by means of a reaction between iodides and peroxyacids, the alkanols yield being equal to 86.5%.

THE PRESENT INVENTION

Object of the present invention is a new process for preparing hydroxyfluoroalkanes of general formula:

$$X-R_f-Y \qquad (I)$$

wherein X and Y, equal or different from each other, are —F or —$CH_2CH(A)OH$ (A is H or an alkyl containing 1 to 3 carbon atoms), X being different from F when Y is F and vice-versa; $R_f$ is a straight or branched perfluoroalkylene chain containing from 2 to 18 carbon atoms, preferably from 4 to 12.

The process comprises reacting in a homogeneous phase compounds of formula:

$$W-R_f-T \qquad (II),$$

where $R_f$ is the same as defined hereinabove and W and T, equal or different from each other, are —F, —$CH_2CH(A)I$ (A is H or an alkyl having 1 to 3 carbon atoms), W being different from F when T is F and vice-versa, with water—in an organic solvent, completely miscible with water or in which water is soluble for at least 1.7% by weight at 20° C., in the presence of catalysts comprising one or more transition metal ions. Preferred metal ions are those having an atomic number from 24 to 29, from 44 to 47, from 74 to 79 and those having as atomic number of 42 and 58. More preferred are Cu, Fe, Co, Ni, Ag.

Useful transition metal compounds are hydrated salts and oxides, both those which are fully soluble and those which are little soluble in the reaction medium. Preferred compounds are the ones whose anion has low basic and nucleophile properites; for example, sulphates, nitrates, phosphates, fluoborates can be used.

Preferred organic solvents are $CH_3CN$, DMF, DMSO, $CH_3COOH$, $CH_3NO_2$, in particular $CH_3CN$, DMF, DMSO.

The process temperature ranges from 120° C. to 280° C., preferably from 140° C. to 200° C.

The time required depends on the specific reagents and on the temperature; generally it is of the order of a few hours. Longer times, even much longer times, do not detrimentally affect the reaction selectivity.

The reaction takes place under an autogenous pressure.

The metal concentration expressed as gram atoms of metal/gram atoms of iodine ratio is lower than 0.1, preferably lower than 0.01 and at least of 0.0005.

The amount of $H_2O$ expressed as mols of $H_2O$/gram atoms of iodine ratio ranges from 1 to 100, preferably from 2 to 30.

The $H_2O$/organic solvent volume ratio ranges preferably from 0.1 to 1.2.

Examples of utilizable iodofluoroalkanes are the ones obtained by addition of ethylene or alpha-olefins to the iodoperfluoroalkanes described in Italian patent applications Nos. 19,652 A/85 and 20,235 A/85, in U.S. Pat. No. 3,514,487 and in DOS No. 2,054,922.

The yields obtained through the reaction carried out according to the process of the invention are very high, generally of at least 95%. Also the selectivity is very high; in particular, the dehydrohalogenation products having unsaturated end groups are either absent or present only as traces.

The process of the invention utilizes metal ions which do not rise pollution problems and are little expensive.

Said metal ions are utilized in little amounts, that being a further improvement with respect to the prior art, according to which, for similar reactions, metal ion salts were utilized in stoichiometric amounts.

Another advantage of the process of the present invention is that iodine, which is contained in the starting compounds, after the reaction is present at hydriodic acid, which is easy to recover, what results in at economic advantage.

When the starting compound has an end group of formula:

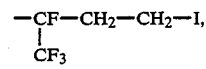

it is possible to keep unaltered this group and to substitute only the other iodine atom by the hydroxy group, so obtaining a product, which is utilizable for subsequent asymmetric reactions.

A particular feature of the present invention which represents still a further advantage with respect to the art resides in the fact that it is possible to synthetize the compounds of type (II) directly in the reaction medium of the process of the invention, by addition of ethylene or alpha-olefins to iodoperfluoroalkanes.

The hydroxyfluoroalkanes prepared according to the process of the invention are useful as intermediates for preparing products utilized in the treatment of textiles in order to impart oil- and water-repellency to them.

In particular, said hydroxyfluoroalkanes are converted to esters by unsaturated carboxylic acids, and then are polymerized.

The following examples are given to illustrate the present invention, but are not to be considered at a limitation thereof.

EXAMPLE 1

Two-step synthesis (A) Precursor preparation.

Into a 5-liter pressure reactor of AISI 316 were charged 1.15 kg of $C_4F_8I_2$ (2.53 moles), 25.2 g of CuI (0.10 moles) in 2 l of acetonitrile.

The reactor was closed and purged with $N_2$.

The pressure was brought to 64 atm. by means of ethylene.

The temperature was gradually brought to 160° C. and the whole was allowed to stand for 8 hours. After cooling to room temperature, ethylene in excess was discharged, the reactor was then opened and water was added until a white precipitate was obtained. It was filtered and vacuum-dried at 70° C. The rough precipitate was purified by crystallization from hexane. Obtained were 1.26 kg of product. On the basis of the analytical data (G.C., N M R $^{19}F$, N M R $^1H$) the product resulted to be:

$$ICH_2CF_2(CH_2)_4CH_2CH_2I.$$

The crystallized product yield was equal to 98%.

(B) Hydrolysis reaction.

Into an Inconel 5-liter autoclave there were charged 1.00 kg of the product obtained from step (A) (1.96 moles) and 16.35 g of $CuSO_4.5H_2O$ (0.066 moles), 1.8 l of acetonitrile and 1 liter of $H_2O$. It was heated to 160° C. under intense stirring and this temperature was maintained for about 12 hours. After cooling to room temperature, the reactor content was treated with water in excess until complete separation of a heavy phase. The mother liquors were repeatedly extracted with ethyl ether which, in turn, was joined to the preceding phase. The solvents were removed under reduced pressure. The residue was treated with 200 ml of 10% NaOH at 70° C. for 2 hours.

The organic phase was separated and washed with water; the mother liquors, in turn, were extracted with ether. The ethereal phase was joined to the previously separated organic phase.

Ether was separated by fractioned distillation. The residue was distilled under reduced pressure: obtained were 540 g of a white crystalline solid which, subjected to analyses (NMR $^{19}F$, NMR $^1H$) resulted to be:

$$\overset{d\ \ \ c\ \ \ b\ \ \ a}{HOCH_2CH_2CF_2CF_2CF_2CF_2CH_2CH_2OH.}$$

where the chemical shift values (relating to TMS and $CCl_3F$) were as follows:
a = 3.9 ppm (triplet)
b = 2.3–2.6 ppm (multiplet)
c = −113.5 ppm
d = −123.5 ppm On G.C. analysis, the product revealed one peak only.

The reaction yield was of 96%.

EXAMPLE 2

One-step synthesis

Into the same reactor of example 1, step (B) and following the same operative modalities there were changed 870 g of $C_6F_{12}I_2$ (1.57 moles), 15.6 g of $CuSO_4.5H_2O$ (0.063 moles), 1.8 l of acetonitrile and 1 l of water. Ethylene was then let in till reaching 52 atm.

The whole was gradually brought to 160° C., and this temperature was maintained for 12 hours under intense stirring. It was cooled down to room temperature, and following the modalities of example 1, step B), 585 g of a crystalline solid were obtained, which, subjected to analyses (NMR $^1H$, NMR $^{19}F$), resulted to be:

$$\overset{e\ \ \ \ d\ \ \ c\ \ \ b\ \ \ a}{HOCH_2CH_2CF_2CF_2CF_2CF_2CF_2CF_2CH_2CH_2OH.}$$

where the chemical shift values relating to TMS and $CCl_3F$ were:
a = 3.9 ppm (triplet)
b = 2.3–2.6 ppm (multiplet)
c = −113.5 ppm
d = −123.5 ppm
e = −121.5 ppm.

The G.C. analysis revealed the presence of a unique peak.

The crystallized product yield was equal to 95.6%.

EXAMPLE 3

Into the reactor of example 1, step B) and according to the same operative modalities there were charged 900 g of a mixture of $C_6F_{12}I_2$ (40%) and $C_8F_{16}I_2$ (60%) equal to 1.47 moles, 14.6 g of $CuSO_4.5H_2O$ (0.059 moles), 1.8 l of acetonitrile and 1 l of $H_2O$. Ethylene was then introduced until a pressure of 50 atm. was attained.

The reactor was gradually brought to 165° C. and it was maintained at this temperature during about 15 hours.

It was cooled to room temperature, whereafter it was operated as in Example 1, step B).

After crystallization from hexane, 640 g of a white solid product were obtained. Gaschromatographic analyses showed two peaks (the areas of which were in the ratio of 2:3 to each other), the first of which corresponded to the product of Example 2. From the spectroscopic analysis (NMR $^{19}F$, NMR $^1H$) it resulted that the final product was composed of:

$$40\%\ HOCH_2CH_2CF_2CF_2CF_2CF_2CF_2CF_2CH_2CH_2OH,$$

$$60\%\ \overset{f\ \ \ e\ \ \ d\ \ \ c\ \ \ b\ \ \ a}{HOCH_2CH_2CF_2CF_2CF_2CF_2CF_2CF_2CF_2CF_2CH_2CH_2OH,}$$

where the chemical shift values relating to TMS and $CCl_3F$ were the following:
a = 3.9 ppm (triplet)
b = 2.3–2.6 ppm (multiplet)
c = −113.5 ppm
d = −123.5 ppm
e,f = −121.5 ppm.

The yield was equal to 98%.

EXAMPLE 4

Into a pressure reactor of 250 ml volume, made of Monel, there were introduced 50 g of $$\underset{CF_3}{\overset{|}{I(CF_2)_5CFI}}$$

(0.083 moles), 0.825 g of $CuSO_4.5H_2O$ (0.0033 moles) in 110 ml of acetonitrile and 30 ml of water.

The reactor was closed and air present therein was let off; ethylene was introduced up to a pressure of 60 atm.

The reactor was brought to 180° C. and it was allowed to stand for about 15 hours under intense stirring.

It was cooled down to room temperature and, operating as is described in Example 1, step B), a colorless liquid product was obtained which, on gaschromatographic and spectrographic analyses (NMR $^{19}$F and NMR $^1$, proved to be composed of:

$$14\% \quad \overset{m}{HOCH_2}\overset{l}{CH_2}\overset{i}{CF_2}\overset{h}{CF_2}\overset{g}{CF_2}\overset{f}{CF_2}\overset{ed}{CF_2}\overset{CF_3}{\underset{|}{C}}F\overset{c}{CH_2}\overset{b}{CH_2}\overset{a}{I}$$

| | | | | |
|---|---|---|---|---|
| a | = | 3.4 | ppm | (triplet) |
| b | = | 2.8–3.1 | ppm | (multiplet) |
| c | = | −182.5 | ppm | |
| d | = | −75 | ppm | |
| e | = | −117 | ppm | |
| f,g | = | −121.5 | ppm | |
| h | = | −123.5 | ppm | |
| i | = | −113.5 | ppm | |
| l | = | 2.3–2.6 | ppm | (multiplet) |
| m | = | 3.9 | ppm | (triplet) |

$$86\% \quad HOCH_2CH_2CF_2CF_2CF_2CF_2CF_2\overset{dCF_3}{\underset{|}{C}}FCH_2CH_2OH,$$
$$\quad\quad m\quad l\quad\quad i\quad\quad h\quad\quad g\quad\quad f\quad\quad e\quad\quad\quad c\quad b\quad a$$

| | | | | |
|---|---|---|---|---|
| a | = | 3.75 | ppm | (triplet) |
| b | = | 2.1–2.4 | ppm | (multiplet) |
| c | = | −186.5 | ppm | |
| d | = | −76 | ppm | |
| e | = | −117 | ppm | |
| f,g | = | −121.5 | ppm | |
| h | = | −123.5 | ppm | |
| i | = | −113.5 | ppm | |
| l | = | 2.3–2.6 | ppm | (multiplet) |
| m | = | 3.9 | ppm | (triplet) |

EXAMPLE 5

Into the reactor of example 4 and according to the same operative modalities there were introduced 23 g of $C_4F_8I_2$ (0.05 moles), 0.64 g of $FeSO_4.7H_2O$ (0.0023 moles), 60 ml of $CH_3CN$ and 40 ml of water. Ethylene was let in until a pressure of 60 atm was attained. It was heated to 160° C. for 12 hours under stirring. The product was recovered as in Example 4; obtained were 13.9 g of a white solid product which, subjected to GC and NMR analyses, resulted to be:

$$HOCH_2CH_2(CF_2)_4CH_2CH_2OH.$$

The reaction yield was of 96%.

EXAMPLE 6

Into an Inconel pressure reactor of 250 ml volume there were charged 31 g of $ICH_2CH_2(CF_2)_4CH_2CH_2I$ (0.06 moles), 0.920 g of $CuSO_4.5H_2O$ (0.0037 moles), 60 ml of dimethylsulphoxide and 40 ml of water. The reactor was closed and purged with $N_2$, then it was heated to 165° C. for 14 hours under stirring. By operating according to the modalities already described in Example 1, step (B), with the exception of the treatment with soda, there were obtained 16.7 g of a white solid product which, on the basis of the analyses (GC and NMR), resulted to be:

$$HOCH_2CH_2(CF_2)_4CH_2CH_2OH.$$

The head fraction contained also traces of olefin:

$$HOCH_2CH_2(CF_2)_4CH_2{=}CH_2.$$

The reaction yield was of 96%.

EXAMPLE 7

The preceding example was repeated, but instead of dimethylsulphoxide an equal amount of N,N-dimethylformamide was utilized. Obtained were 16.9 g of:

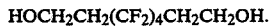

$$HOCH_2CH_2(CF_2)_4CH_2CH_2OH.$$

The reaction yield was of 97%.

EXAMPLE 8

Example 6 was repeated, with the exception that instead of dimethylsulphoxide, an equal amount of acetic acid was used. Obtained were 16.3 g of:

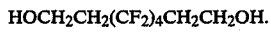

$$HOCH_2CH_2(CF_2)_4CH_2CH_2OH.$$

The reaction yield was of 94%.

EXAMPLE 9

Example 6 was repeated, with the difference that instead of dimethylsulphoxide, an equal amount of nitromethane was used. Obtained were 16.6 g of:

$$HOCH_2CH_2(CF_2)_4CH_2CH_2OH.$$

The reaction yield was of 95%.

EXAMPLE 10

4.8 g of 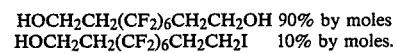 I—$CH_2$—$CH_2$—$(CF_2)_6$—$CH_2$—$CH_2$—I (0.0078 moles) were mixed in a closed glass reactor with 8 ml of acetonitrile, 8 ml of $H_2O$ and 80 mg of silver acetate.

The reactor was purged with $N_2$.

The temperature was brought to 165° C. and this temperature was maintained for 16 hours.

It was cooled down to room temperature, whereafter it was operated as in Example 1, step (B).

The product, under IR and NMR analyses, resulted to be composed of:

$HOCH_2CH_2(CF_2)_6CH_2CH_2OH$ 90% by moles
$HOCH_2CH_2(CF_2)_6CH_2CH_2I$ 10% by moles.

What is claimed is:

1. A process for preparing hydroxyfluoroalkanes of general formula:

$$X\text{-}R_f\text{-}Y \qquad (I)$$

wherein X and Y, equal or different from each other, are —F or —$CH_2CH(A)OH$ (A is H or an alkyl with 1 to 3 carbon atoms) X being different from F when Y is F, and viceversa, $R_f$ is a straight or branched perfluoroalkylene chain containing 2 to 18 carbon atoms, said process comprising reacting in a homogeneous phase compounds of formula:

$$W\text{-}R_f\text{-}T \qquad (II)$$

where $R_f$ is the same as defined hereinabove and W and T, equal or different from each other, are —F, —$CH_2CH(A)I$ (A is H or an alkyl having 1 to 3 carbon atoms), W being different from F when T is F, and vice-versa, with water —in an organic solvent, which is fully miscible with water or in which water is soluble for at least 1.7% by weight at 20° C., in the presence of catalysts comprising one or more transition metal ions having an atomic number ranging from 24 to 29, from 44 to 47, from 74 to 79, and the ones with atomic number 42 and 58.

2. The process according to claim 1, wherein the metal is selected from Cu, Fe, Co, Ni, Ag.

3. The process according to claim 1, wherein the reaction temperature ranges from 120° C. to 280° C.

4. The process according to claim 1, wherein the organic solvent is selected from $CH_3CN$, DMF, DMSO, $CH_3COOH$, $CH_3NO_2$.

5. The process according to claim 1, wherein the compounds of type (II) are directly synthetized in the reaction medium by addition of ethylene or of alpha-olefins to the corresponding iodoperfluoroalkanes.

* * * * *